(12) United States Patent
Naito et al.

(10) Patent No.: US 10,738,019 B2
(45) Date of Patent: Aug. 11, 2020

(54) COMPOUND INCLUDING BASIC DYE AND AMINO ACID, HAIR DYEING DYE, AND HAIR DYEING COMPOSITION

(71) Applicant: HODOGAYA CHEMICAL CO., LTD., Tokyo (JP)

(72) Inventors: Keigo Naito, Tokyo (JP); Yasuaki Miyazaki, Tokyo (JP); Shigetaka Numazawa, Tokyo (JP); Katsumi Abe, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/553,561

(22) Filed: Aug. 28, 2019

(65) Prior Publication Data

US 2020/0071283 A1 Mar. 5, 2020

(30) Foreign Application Priority Data

Aug. 31, 2018 (JP) .................. 2018-162579

(51) Int. Cl.

| | | |
|---|---|---|
| *A61Q 5/10* | (2006.01) |
| *C07D 265/38* | (2006.01) |
| *A61K 8/41* | (2006.01) |
| *A61K 8/42* | (2006.01) |
| *A61K 8/49* | (2006.01) |
| *A61Q 5/06* | (2006.01) |
| *C07C 211/50* | (2006.01) |
| *C07C 233/47* | (2006.01) |
| *C07C 245/08* | (2006.01) |
| *C07D 233/88* | (2006.01) |

(52) U.S. Cl.
CPC ............ *C07D 265/38* (2013.01); *A61K 8/415* (2013.01); *A61K 8/416* (2013.01); *A61K 8/42* (2013.01); *A61K 8/4946* (2013.01); *A61Q 5/065* (2013.01); *C07C 211/50* (2013.01); *C07C 233/47* (2013.01); *C07C 245/08* (2013.01); *C07D 233/88* (2013.01); *A61K 2800/4322* (2013.01)

(58) Field of Classification Search
CPC ........ A61Q 5/065; A61K 8/49; A61K 8/4946; A61K 8/416; A61K 2800/43; A61K 2800/432; A61K 8/44; A61K 8/411; A61K 8/42; A61K 8/442; A61K 2800/4322; C07D 233/88; C07C 245/08; C07C 233/47

See application file for complete search history.

(56) References Cited

U.S. PATENT DOCUMENTS

| | | | |
|---|---|---|---|
| 6,616,708 B2 * | 9/2003 | Ohashi ................... | A61K 8/416 8/405 |
| 2013/0340182 A1 | 12/2013 | Isobe et al. | |
| 2016/0152831 A1 | 6/2016 | Akiba et al. | |
| 2017/0354581 A1 * | 12/2017 | Consoli .................. | A61K 8/411 |

FOREIGN PATENT DOCUMENTS

| | | |
|---|---|---|
| EP | 2 471 503 A1 | 7/2012 |
| EP | 2 471 505 A1 | 7/2012 |
| JP | 2004-269400 A | 9/2004 |
| JP | 2010-001278 A | 1/2010 |
| JP | 2017-088502 A | 5/2017 |
| WO | WO-2010/074717 A2 | 7/2010 |
| WO | WO-2010/074717 A3 | 7/2010 |
| WO | WO-2013/190774 A1 | 12/2013 |
| WO | WO-2014-203771 A | 12/2014 |

OTHER PUBLICATIONS

STIC Search Report dated Mar. 2, 2020.*
European Search Report dated Jan. 20, 2020 in European Application No. 19 194 510.4.

* cited by examiner

*Primary Examiner* — Eisa B Elhilo
(74) *Attorney, Agent, or Firm* — Saliwanchik, Lloyd & Eisenschenk

(57) ABSTRACT

There is provided a compound represented by the following general formula (1).

[Chem. 1]

$$(X)(Z) \qquad (1)$$

(in which, X represents a basic dye having at least one amino group having 0 to 20 carbon atoms which may have a substituent, and
Z represents a non-coloring anion including an amino acid.)

12 Claims, No Drawings

COMPOUND INCLUDING BASIC DYE AND AMINO ACID, HAIR DYEING DYE, AND HAIR DYEING COMPOSITION

CROSS REFERENCE TO RELATED APPLICATION

This application claims priority to Japanese Application No. 2018-162579, filed Aug. 31, 2018; which is hereby incorporated by reference in its entirety.

BACKGROUND

The present disclosure relates to a compound including a basic dye and an amino acid, a hair dyeing dye, and a hair dyeing composition. More specifically, the present disclosure relates to a hair dyeing dye and a hair dyeing composition that have an excellent hair dyeing power, favorable water solubility and foaming property, and excellent sweat resistance, and are capable of effectively suppressing the fading of dyed hair while maintaining the smooth hair during washing and after drying.

In recent years, an increasing number of people in a wide range of ages enjoy various hair colors by dyeing black hair or white hair, and many hair colorings (referred to also as "hair dyes" in some cases), hair manicures, hair color treatments, and color rinses are on the market as hair dyes. In the hair dyeing process, an oxidation hair dye (permanent hair dye) using an oxidation dye having a high hair dyeing power and favorable color durability has been mainly used, but the oxidation hair dye has had a problem that skin irritation such as hair damage and allergy is likely to occur. In view of the above, a hair dye using a basic dye with high safety instead of the above-mentioned oxidation dye has been proposed (see Japanese Patent Application Laid-open No. 2004-269400, Japanese Patent Application Laid-open No. 2010-1278, Japanese Patent Application Laid-open No. 2017-88502, WO 2013/190774, and WO 2014/203771).

A semi-permanent hair dye (hair color treatment or color rinse) using the above-mentioned basic dye has a problem that the dyeing is faded due to daily shampoo, sunburn, or the like, and it has been necessary to repeat hair dyeing many times in order to maintain the dyeing. Repeated hair dyeing significantly damages hair, which may cause fading more easily, and it is an important issue to develop a basic dye or the like having the effect of suppressing the fading.

SUMMARY

It is desired to provide a hair dyeing dye and a hair dyeing composition that have an excellent hair dyeing power, favorable water solubility and foaming property, and excellent sweat resistance, and suppress the fading of dyed hair while maintaining the smooth hair during washing and after drying.

Solution to Problem

The present disclosure has been obtained as a result of intensive studies to solve the above-mentioned problem, the gist of the present disclosure is as follows, and the present disclosure includes the following content.

1. A compound represented by the following general formula (1).

[Chem. 1]

$$(X)(Z) \tag{1}$$

(in which, X represents a basic dye having at least one amino group having 0 to 20 carbon atoms which may have a substituent, and Z represents a non-coloring anion including an amino acid.)

2. The compound in which X in the general formula (1) represents a basic dye represented by the following general formula (2).

[Chem. 2]

$$R^1-N=N-R^2 \tag{2}$$

(in which, $R^1$ and $R^2$ each independently represent an amino group having 0 to 20 carbon atoms which may have a substituent, a linear or branched alkenyl group having 2 to 20 carbon atoms which may have a substituent, an aromatic hydrocarbon group having 6 to 30 carbon atoms which may have a substituent, or a heterocyclic group having 2 to 30 carbon atoms which may have a substituent.)

3. The compound in which X in the general formula (1) represents a basic dye represented by the following general formula (3).

[Chem. 3]

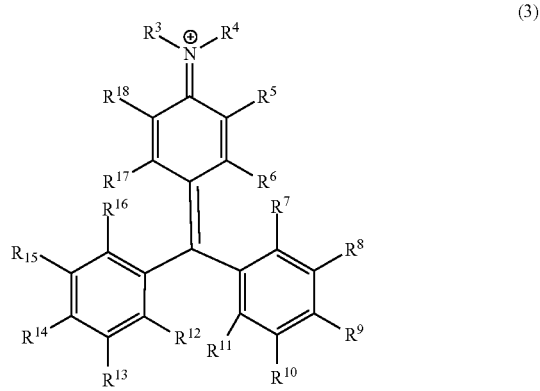

(in which, $R^3$ to $R^{18}$ each independently represent —H, a halogen atom, —NO₂, —NO, —CN, —OH, an amino group having 0 to 20 carbon atoms which may have a substituent, a linear or branched alkenyl group having 2 to 20 carbon atoms which may have a substituent, a linear or branched alkyl group having 1 to 20 carbon atoms which may have a substituent, a cycloalkyl group having 3 to 20 carbon atoms which may have a substituent, a linear or branched alkoxy group having 1 to 20 carbon atoms which may have a substituent, a cycloalkoxy group having 3 to 20 carbon atoms which may have a substituent, an acyl group having 0 to 20 carbon atoms which may have a substituent, an aromatic hydrocarbon group having 6 to 30 carbon atoms which may have a substituent, or a heterocyclic group having 2 to 30 carbon atoms which may have a substituent, and adjacent groups of $R^3$ to $R^{18}$ may be bonded to each other to form a ring.)

4. The compound in which

X in the general formula (1) represents a basic dye represented by the following general formula (4).

[Chem. 4]

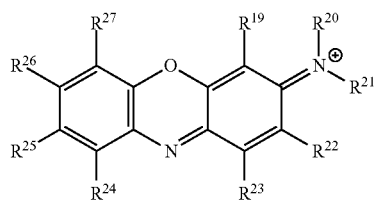

(4)

(in which, $R^{19}$ to $R^{27}$ each independently represent —H, a halogen atom, —NO$_2$, —NO, —CN, —OH, an amino group having 0 to 20 carbon atoms which may have a substituent, a linear or branched alkenyl group having 2 to 20 carbon atoms which may have a substituent, a linear or branched alkyl group having 1 to 20 carbon atoms which may have a substituent, a cycloalkyl group having 3 to 20 carbon atoms which may have a substituent, linear or branched alkoxy group having 1 to 20 carbon atoms which may have a substituent, a cycloalkoxy group having 3 to 20 carbon atoms which may have a substituent, acyl group having 1 to 20 carbon atoms which may have a substituent, aromatic hydrocarbon group having 6 to 30 carbon atoms which may have a substituent, or a heterocyclic group having 2 to 30 carbon atoms which may have a substituent, and adjacent groups of $R^{19}$ to $R^{23}$ and $R^{24}$ to $R^{27}$ may be bonded to each other to form a ring.)

5. The compound in which

X in the general formula (1) represents a basic dye represented by the following general formula (5).

[Chem. 5]

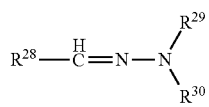

(5)

(in which, $R^{28}$ to $R^{30}$ each independently represent an amino group having 0 to 20 carbon atoms which may have a substituent, a linear or branched alkenyl group having 2 to 20 carbon atoms which may have a substituent, a linear or branched alkyl group having 1 to 20 carbon atoms which may have a substituent, a cycloalkyl group having 1 to 20 carbon atoms which may have a substituent, a linear or branched alkoxy group having 1 to 20 carbon atoms which may have a substituent, a cycloalkoxy group having 3 to 20 carbon atoms which may have a substituent, an acyl group having 1 to 20 carbon atoms which may have a substituent, an aromatic hydrocarbon group having 6 to 30 carbon atoms which may have a substituent, or a heterocyclic group having 2 to 30 carbon atoms which may have a substituent, and $R^{29}$ and $R^{30}$ may be bonded to each other to form a ring.)

6. The compound in which the non-coloring anion including an amino acid represented by Z in the general formula (1) is an amino acid anionic surfactant.

7. A hair dyeing dye including the compound.

8. A hair dyeing composition, including:

the hair dyeing dye;

an auxiliary selected from the group consisting of a wetting agent, a swelling agent, a penetrating agent, a solvent, a pH adjusting agent, a surfactant, a fragrance, and a thickener; and water.

Advantageous Effects of Invention

In accordance with the compound and the hair dyeing dye according to the present disclosure, it is possible to provide a hair dyeing composition that has an excellent hair dyeing power, favorable water solubility and foaming property, and excellent sweat resistance, and suppress the fading of dyed hair while maintaining the smooth hair with no hair roughness and no hair irregularity during washing and after drying.

These and other objects, features and advantages of the present disclosure will become more apparent in light of the following detailed description of best mode embodiments thereof, as illustrated in the accompanying drawings.

DETAILED DESCRIPTION OF EMBODIMENTS

Hereinafter, an embodiment of the present disclosure will be described in detail. Note that the present disclosure is not limited the embodiment below, and various modifications can be made without departing from the essence of the present disclosure. First, the compound represented by the general formula (1) will be specifically described. However, the present disclosure is not limited thereto.

In the general formula (1), the "basic dye" in the "basic dye having at least one amino group having 0 to 20 carbon atoms which may have a substituent" represented by "X" is referred to also as a cationic dye, and the basic dye indicates a dye including a compound having an onium group showing basic (cationic) properties in the molecular structure. Examples of the onium group contained in a dye molecule represented by "X" include an ammonium group (—NH$_3^+$), a phosphonium group (—PH$_3^+$), an oxonium group (—OH$_2^+$), a sulfonium group (—SH$_2^+$), an iminium group (=NH$_2^+$), and a nitrilium group (—C≡NH$^+$), and typical ones have groups relating to the following quaternary ammonium groups. The "—H" part in these groups may be substituted with another group such as a linear or branched alkyl group or aromatic hydrocarbon group having 1 to 20 carbon atoms which may have a substituent. One dye molecule may include one or more of any of these groups. Further, the basic dye "X" is favorably a water-soluble dye.

Examples of the "amino group" in the "basic dye having at least one amino group having 0 to 20 carbon atoms which may have a substituent" represented by "X" in the general formula (1) include a quaternary ammonium group (—N$^+$RR'R"R, R' and R" are each H or an arbitrary substituent), "=N$^+$<" or "=N$^+$RR'" (R and R' are each H or any substituent), an unsubstituted amino group (—NH$_2$), a monosubstituted amino group (—NHR, R is an arbitrary substituent), and a disubstituted amino group (—NHRR', R and R' are each an arbitrary substituent). However, a basic dye containing no acidic group such as a sulfonic acid group (—SO$_3$H), a carboxyl group (—COOH), a phosphate group (—O—PO(OH)$_2$), a hydroxamic acid group (—CO—NH—OH), a phosphonic acid group (—PO(OH)$_2$), a boric acid group (—O—B(OH)$_2$), a phosphonic acid group (—O—POH$_2$), and a silanol group (—SiH$_2$—OH or —Si(OH)$_3$) is favorable.

In the general formula (1), "Z" represents "a non-coloring anion including an amino acid". "Z" in the general formula (1) is a counter ion of the "X", and can form a compound (complex) represented by the general formula (1). The "non-coloring anion containing an amino acid" in an embodiment of the present disclosure represents an "amino acid" or a compound that has the structure of "amino acid" and is capable of becoming an anion. In general, the amino acid is a compound having an amino group (—NRR', R and R' each represent H or an arbitrary group which may be the same or differs) and a carboxyl group (—COOH, —COO$^-$). Specific examples of the amino acid (α-amino acid) mainly include glycine, alanine, valine, leucine, isoleucine, serine, threonine, cysteine, cystine, methionine, aspartic acid, glutamic acid, asparagine, glutamine, lysine, arginine, phenylalanine, tyrosine, tryptophan, and histidine. The "non-coloring anion containing an amino acid" in the embodiment of the present disclosure may contain the amino acid in the molecular structure, and therefore may have a structure in which the amino group or the like in the amino acid is substituted.

In the general formula (1), "Z" may include one or more of the amino group and carboxyl group. In the case where the "non-coloring anion containing an amino acid" represented by "Z" is in the "anionic" state, "Z" is an anion that forms a complex with the cation "X". Therefore, the valence of "X" and the valence of "Z" are favorably equal to each other, and are each more favorably monovalent or divalent, and particularly favorably monovalent.

In (X)(Z) represented by the general formula (1), "X" and "Z" may each be one type or mixture of a plurality of types so that the general formula (1) is neutral as a whole. However, the number of types of X is favorably one. Similarly, the number of types of "Z" is favorably one.

In the general formula (1), a commercially available basic dye can be used as "X". Further, in the general formula (1), "X" is favorably a compound represented by any of the general formulae (2) to (5).

In the general formula (1), examples of the "amino group having 0 to 20 carbon atoms which may have a substituent" contained in "X" or represented by $R^1$ to $R^{30}$ include a monosubstituted amino group such as —NH$_2$, an ethylamino group, an acetylamino group, and a phenylamino group, and a disubstituted amino group such as a diethylamino group, a diphenylamino group, and an acetylphenylamino group. In addition, a trialkylamino (trialkylammonio) group such as a trimethylamino (or trimethylammonio) group and a triethylamino (or triethylammonio) group, and a quaternary ammonium group which may have a substituent such as a triphenylamino (or trimethylammonio) group obtained by further bonding a group to these amino groups are also included in examples of the "amino group having 0 to 20 carbon atoms which may have a substituent", and these substituents may be the same or different from each other.

In the general formula (1), specific examples of the "linear or branched alkenyl group having 2 to 20 carbon atoms" in the "linear or branched alkenyl group having 2 to 20 carbon atoms which may have a substituent" represented by $R^1$ to $R^{30}$ include a vinyl group, an allyl group, an isopropenyl group, a 2-butenyl group, 1-hexenyl group, and a linear or branched group in which a plurality of these alkenyl groups are bonded.

In the general formula (1), specific examples of the "aromatic hydrocarbon group having 6 to 30 carbon atoms" in the "aromatic hydrocarbon group having 6 to 30 carbon atoms which may have a substituent" represented by $R^1$ to $R^{30}$ include a phenyl group, a biphenylyl group, a terphenylyl group, a tetrakisphenyl group, a styryl group, a naphthyl group, an anthryl group, an acenaphthenyl group, a phenanthryl group, a fluorenyl group, an indenyl group, a pyrenyl group, and a triphenylenyl group, and an acyl group or an amino group may be interposed. Note that the "aromatic hydrocarbon group" in the embodiment of the present disclosure indicates an aromatic hydrocarbon group and a condensed polycyclic aromatic group.

In the general formula (1), specific examples of the "heterocyclic group having 2 to 30 carbon atoms" in the "heterocyclic group having 2 to 30 carbon atoms which may have a substituent" represented by $R^1$ to $R^{30}$ include a triazinyl group, a pyridyl group, a pyrimidinyl group, an imidazolyl group, a furanyl group, a pyrrolyl group, a thienyl group, a quinolyl group, an isoquinolyl group, a benzofuranyl group, a benzothienyl group, an indolyl group, a carbazolyl group, a carbolinyl group, a pyridoindolyl group, an oxazolyl group, a benzoxazolyl group, a thiazolyl group, a benzothiazolyl group, a quinoxalyl group, a benzimidazolyl group, a pyrazolyl group, a dibenzofuranyl group, a dibenzothienyl group, a naphthyridinyl group, a phenanthrolinyl group, an acridinyl group, and a hydantoin group, and an acyl group or an amino group may be interposed.

In the general formulae (3) and (4), examples of the "halogen atom" represented by $R_3$ to $R_{27}$ include a fluorine atom, a chlorine atom, a bromine atom, and an iodine atom. In the embodiment of the present disclosure, as the "halogen atom", a fluorine atom or a chlorine atom is favorable.

In the general formulae (3) to (5), specific examples of the "linear or branched alkyl group having 1 to 20 carbon atoms" in the "linear or branched alkyl group having 1 to 20 carbon atoms which may have a substituent" represented by $R^3$ to $R^{30}$ include: a linear alkyl group such as a methyl group, an ethyl group, an n-propyl group, a butyl group, a pentyl group, a hexyl group, a heptyl group, an octyl group, a nonyl group, and a decyl group; and a branched alkyl group such as an isopropyl group, an isobutyl group, an s-butyl group, a t-butyl group, an isooctyl group, and a t-octyl group.

In the general formulae (3) to (5), specific examples of the "cycloalkyl group having 3 to 20 carbon atoms" in the "cycloalkyl group having 3 to 20 carbon atoms which may have a substituent" represented by $R^3$ to $R^{30}$ include a cyclopropyl group, a cyclobutyl group, a cyclopentyl group, a cyclohexyl group, a cycloheptyl group, a cyclooctyl group, a cyclodecyl group, and a cyclododecyl group.

In the general formulae (3) to (5), specific examples of the "linear or branched alkoxy group having 1 to 20 carbon atoms" in the "linear or branched alkoxy group having 1 to 20 carbon atoms which may have a substituent" represented by $R^3$ to $R^{30}$ include: a linear alkoxy group such as a methoxy group, an ethoxy group, a propoxy group, an n-butoxy group, an n-pentyloxy group, an n-hexyloxy group, a heptyloxy group, an octyloxy group, a nonyloxy group, and a decyloxy group; and a branched alkoxy group such as an isopropoxy group, an isobutoxy group, an s-butoxy group, a t-butoxy group, an isooctyloxy group, and a t-octyloxy group.

In the general formulae (3) to (5), specific examples of the "cycloalkoxy group having 3 to 20 carbon atoms" in the "cycloalkoxy group having 3 to 20 carbon atoms which may have a substituent" represented by $R^3$ to $R^{30}$ include a cyclopropoxy group, a cyclobutoxy group, a cyclopentyloxy group, and a cyclohexyloxy group.

In the general formulae (3) to (5), specific examples of the "acyl group having 1 to 20 carbon atoms" in the "acyl group having 1 to 20 carbon atoms which may have a substituent" represented by $R^3$ to $R^{30}$ include a formyl group, an acetyl group, a propionyl group, an acrylyl group, and a benzoyl group.

specific examples of the "substituent" in the "amino group having 0 to 20 carbon atoms which has a substituent" in X of the general formula (1) or the "substituent" in the "amino group having 0 to 20 carbon atoms which has a substituent", "linear or branched alkenyl group having 2 to 20 carbon atoms which has a substituent", "linear or branched alkyl group having 1 to 20 carbon atoms which has a substituent", "cycloalkyl group having 3 to 20 carbon atoms which has a substituent", "linear or branched alkoxy group having 1 to 20 carbon atoms which has a substituent", "cycloalkoxy group having 3 to 20 carbon atoms which has a substituent", "acyl group having 1 to 20 carbon atoms which has a substituent", "aromatic hydrocarbon group having 6 to 30 carbon atoms which has a substituent", or "heterocyclic group having 5 to 30 ring-formed atoms which has a substituent" represented by $R^1$ to $R^{30}$ in the general formulae (2) to (5) include: a nitro group (—$NO_2$), a nitroso group (—NO), a cyano group (—CN), a hydroxyl group (—OH);

a halogen atom such as a fluorine atom, a chlorine atom, a bromine atom, and an iodine atom;

an unsubstituted amino group;

a linear or branched alkyl group having 1 to 20 carbon atoms, such as a methylamino group, a dimethylamino group, a diethylamino group, an ethylmethylamino group, a methylpropylamino group, a di-t-butylamino group, and a diphenylamino group, or a mono- or di-substituted amino group including an aryl group having 6 to 30 carbon atoms;

a sulfonamide group (—S(=O)$_2$—NRR') ("—NRR'" in the group represents an unsubstituted amino group; a linear or branched alkyl group having 1 to 20 carbon atoms, such as a methylamino group, a dimethylamino group, a diethylamino group, an ethylmethylamino group, a methylpropylamino group, a di-t-butylamino group, and a diphenylamino group, or a mono- or di-substituted amino group including an aryl group having 6 to 30 carbon atoms);

a linear or branched alkyl group having 1 to 20 carbon atoms, such as a methyl group, an ethyl group, an n-propyl group, an isopropyl group, an n-butyl group, an s-butyl group, a t-butyl group, a pentyl group, an n-hexyl group, an isohexyl group, a heptyl group, an n-octyl group, a t-octyl group, an isooctyl group, a nonyl group, and a decyl group;

a cycloalkyl group having 3 to 20 carbon atoms, such as a cyclopropyl group, a cyclobutyl group, a cyclopentyl group, a cyclohexyl group, a cycloheptyl group, a cyclooctyl group, a cyclodecyl group, and a cyclododecyl group;

a linear or branched alkoxy group having 1 to 20 carbon atoms, such as a methoxy group, an ethoxy group, a propoxy group, a t-butoxy group, an n-pentyloxy group, and an n-hexyloxy group;

a cycloalkoxy group having 3 to 20 carbon atoms, such as a cyclopropoxy group, a cyclobutoxy group, a cyclopentyloxy group, and a cyclohexyloxy group;

a vinyl group, a 1-propenyl group, an allyl group, a 1-butenyl group, a 2-butenyl group, a 1-pentenyl group, a 1-hexenyl group, an isopropenyl group, an isobutenyl group, or a linear or branched alkenyl group having 2 to 20 carbon atoms in which a plurality of these alkenyl groups are bonded;

an acyl group having 1 to 20 carbon atoms, such as a formyl group, an acetyl group, a propionyl group, an acrylyl group, and a benzoyl group;

an aromatic hydrocarbon group having 6 to 30 carbon atoms, such as a phenyl group, a naphthyl group, an anthryl group, a phenanthryl group, a pyrenyl group, a triphenylenyl group, an indenyl group, a fluorenyl group, and a styryl group;

a heterocyclic group having 2 to 30 carbon atoms, such as a pyridyl group, a pyrimidinyl group, a triazinyl group, a pyrrolyl group, an imidazolyl group, a pyrazolyl group, a triazolyl group, a pyrazinyl group, a pyridazinyl group, a piperidinyl group, a piperazinyl group, a quinolyl group, an isoquinolyl group, a naphthyridinyl group, an indolyl group, a benzimidazolyl group, a carbazonyl group, a carbolinyl group, a pyridoindolyl group, an acridinyl group, a phenanthrolinyl group, a phenanthridinyl group, a hydantoin group, a furanyl group, a benzofuranyl group, a dibenzofuranyl group, a pyranyl group, a coumarinyl group, an isobenzofuranyl group, a xanthenyl group, an oxanthrenyl group, a pyranonyl group, a thienyl group, a thiopyranyl group, a benzothienyl group, a dibenzothienyl group, a thioxanthenyl group, an oxazolyl group, a benzoxazolyl group, a morpholinyl group, a thiazolyl group, and a benzothiazolyl group; and a cyclic olefin group having 3 to 30 carbon atoms, such as a cyclopropenyl group, a cyclobutenyl group, a cyclopentenyl group, a cyclohexenyl group, a cycloheptenyl group, a (1,3- or 1,4-) cyclohexadienyl group, and a 1,5-cyclooctadienyl group.

Any of these "substituents" may include only one substituent or a plurality of substituents. In the case where any of the substituents includes a plurality of substituents, the plurality of substituents may be the same or different from each other. Further, these "substituents" may each have the substituent exemplified above. Further, these substituents may be bonded to each other via a single bond, a substituted or unsubstituted methylene group, an oxygen atom, or a sulfur atom to form a ring.

In the general formula (2), as $R^1$ or $R^2$,
an aromatic hydrocarbon group having 6 to 30 carbon atoms which may have a substituent, or
a heterocyclic group having 2 to 30 carbon atoms which may have a substituent is favorable.

In the general formula (3), as $R^3$ to $R^{18}$, —H, a halogen atom, an amino group having 0 to 20 carbon atoms which may have a substituent, or a linear or branched alkyl group having 1 to 20 carbon atoms which may have a substituent is favorable.

In the general formula (3), adjacent groups of $R^3$ to $R^{18}$ may be bonded to each other to form a ring. In the case of forming a ring, it is favorable that $R^3$ and $R^4$, $R^5$ and $R^6$, $R^7$ to $R^{12}$ to $R^{16}$, or $R^{17}$ and $R^{18}$ are bonded to each other to form a ring, and the ring is favorably a 5-membered ring or a 6-membered ring.

In the general formula (4), as $R^3$ to $R^{18}$, —H,
an amino group having 0 to 20 carbon atoms which may have a substituent, or
an aromatic hydrocarbon group having 6 to 30 carbon atoms which may have a substituent is favorable.

In the general formula (4), adjacent groups of $R^{19}$ to $R^{27}$ may be bonded to each other to form a ring. In the case of forming a ring, it is favorable that $R^{20}$ and $R^{21}$, $R^{22}$ and $R^{23}$, or $R^{24}$ to $R^{27}$ may be bonded to each other to form a ring, and the ring is favorably a 5-membered ring or a 6-membered ring.

In the general formula (5), as $R^{28}$ to $R^{30}$,
a linear or branched alkyl group having 1 to 20 carbon atoms which may have a substituent,
an aromatic hydrocarbon group having 6 to 30 carbon atoms which may have a substituent, or
a heterocyclic group having 2 to 30 carbon atoms which may have a substituent is favorable.

In the general formula (5), $R^{29}$ and $R^{30}$ may be bonded to each other to form a ring. In the case of forming a ring, the ring is favorably a 5-membered ring or a 6-membered ring.

In the general formula (1), the "non-coloring anion containing an amino acid" represented by "Z" is favorably an amino acid surfactant that contains an amino acid in the molecular structure. Therefore, it is favorably an amino acid anionic surfactant. Specific examples thereof include
an N-acyl-N-alkylglycine salt (N—$C_8$ to $C_{22}$ alkanoyl-N-alkylglycine salt such as an N-cocoyl-N-methylglycine),
an N-acyl-N-alkylglutamate (N—$C_8$ to $C_{22}$ alkanoyl-N-alkylglutamate such as an N-cocoyl-N-methylglutamate),
an N-acyl-N-alkylalanine salt (N—$C_8$ to $C_{22}$ alkanoyl-N-alkylalanine salt such as an N-cocoyl-N-methylalanine salt and an N-lauroyl-N-methyl-β-alanine salt),
an N-acyl-N-alkylaspartate (N—$C_8$ to $C_{22}$ alkanoyl-N-alkylaspartate such as an N-cocoyl-N-methyl aspartate),
an N-acyl glycine salt (N—$C_8$ to $C_{22}$ alkanoyl glycine salt such as an N-cocoyl glycine salt),
an N-acyl glutamate (N—$C_8$-$C_{22}$ alkanoyl glutamate such as a sodium lauroyl glutamate and an N-cocoyl glutamate),
an N-acylalanine salt (N—$C_8$ to $C_{22}$ alkanoylalanine salt such as an N-cocoylalanine salt),
an N-acyl aspartate (N—$C_8$ to $C_{22}$ alkanoyl aspartate such as an N-lauroyl aspartate), and
an amino acid anion (anionic) surfactant such as an N-acyl sarcosine salt (N—$C_8$ to $C_{22}$ alkanoyl sarcosine salt such as an N-cocoyl sarcosine salt). Examples of the salts include a salt with an alkali metal such as lithium, sodium, potassium, and cesium, a salt with trialkylamine such as triethanolamine, and a salt with a basic amino acid such as arginine.

In the general formula (1), as the amino acid anion surfactant represented by "Z", an N-acyl-N-alkyl glutamate, an N-acyl-N-alkylalanine salt such as an N-lauroyl-N-methyl-β-alanine salt, an N-acyl glutamate such as a sodium lauroyl glutamate, or an N-acylalanine salt is favorable. In these amino acid anion surfactants, examples of the alkyl group in the case where the "N-alkyl" group portion is included include a methyl group, an ethyl group, and a propyl group, and a methyl group is favorable. Further, in the amino acid anion surfactants, examples of the "acyl" group include a cocoyl group, a lauroyl group, a myristoyl group, a palmitoyl group, and a stearoyl group, and a cocoyl group or a lauroyl group is favorable.

Specific examples of favorable compounds as the compound according to the embodiment of the present disclosure represented by the general formula (1) are shown below. However, the present disclosure is not limited to these compounds. Note that in the following structural formulae, some hydrogen atoms are omitted, and the planar structural formula is described even in the case where stereoisomers exist.

[Chem. 6]

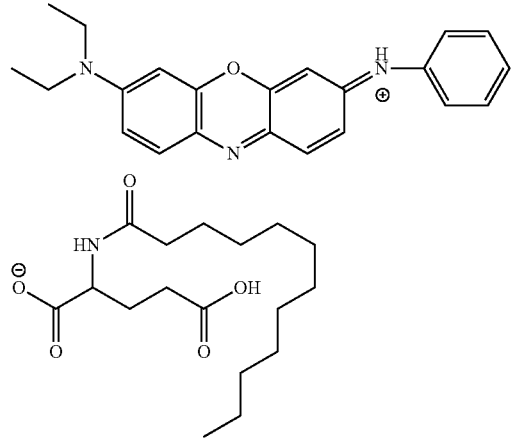

(A-1)

[Chem. 7]

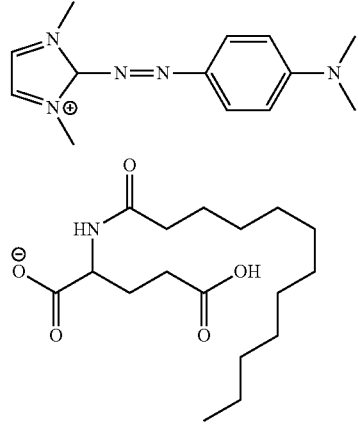

(A-2)

[Chem. 8]

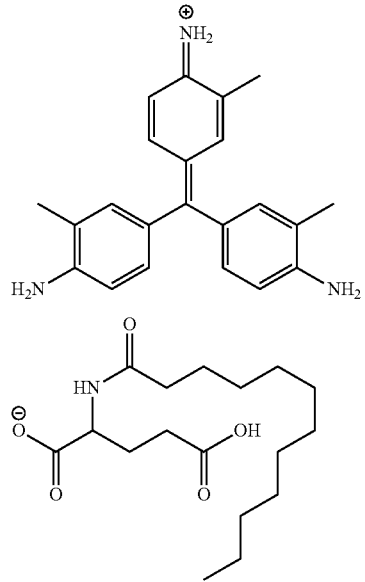

(A-3)

[Chem. 9]
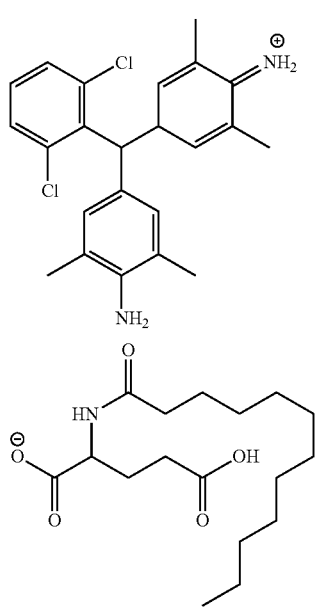
[Chem. 10]
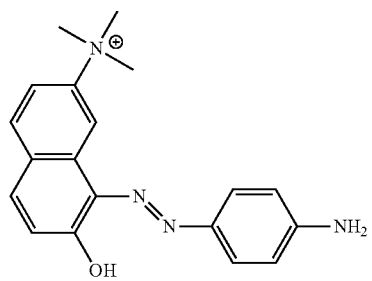
[Chem. 11]
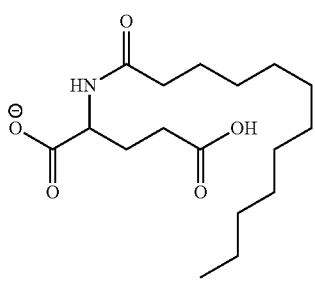
(A-4)
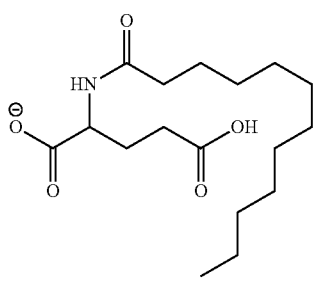
[Chem. 12]
(A-7)
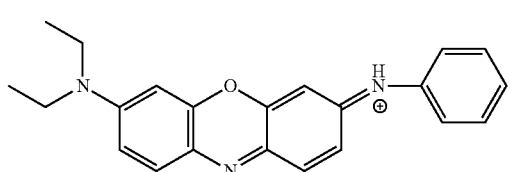
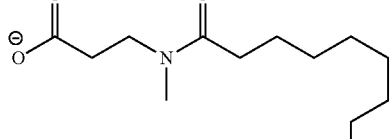
[Chem. 13]
(A-8)
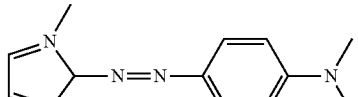
[Chem. 14]
(A-9)
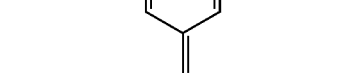

[Chem. 15]

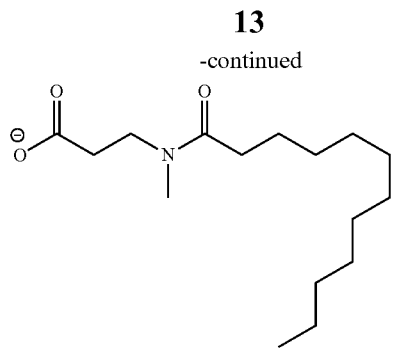

[Chem. 16]

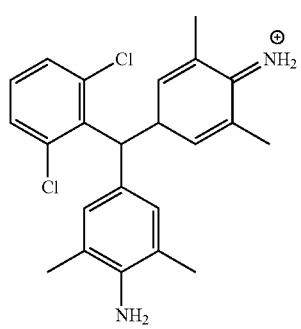

(A-10)

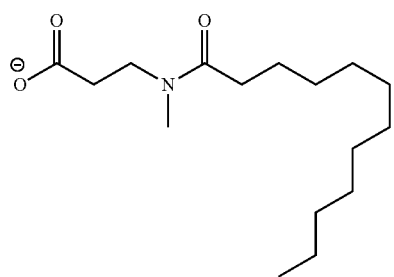

(A-11)

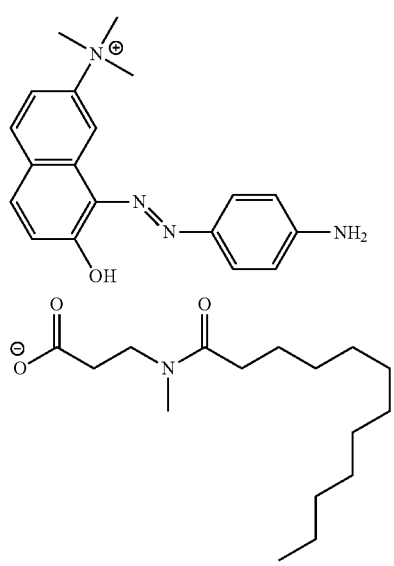

[Chem. 17]

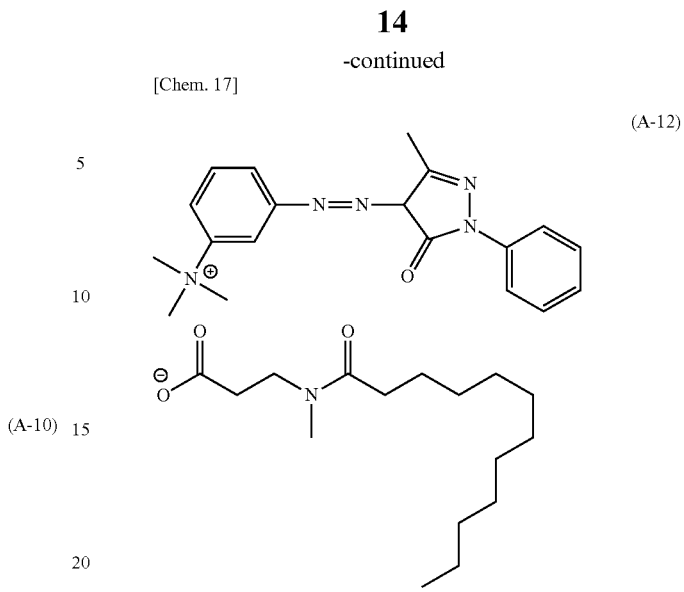

(A-12)

The compound represented by the general formula (1) can be synthesized using, for example, the basic dye represented by (X) in the general formula (1) and a salt such as a sodium salt of an amino acid represented by (Z) as raw materials. Specifically, the compound that is a hair dyeing dye (dye having an amino acid as a counter ion) according to the embodiment of the present disclosure can be obtained by dissolving the basic dye in water, an organic solvent, or the like, adding an amino acid sodium salt or the like and causing the mixture to react with each other under appropriate temperature conditions, and purifying the obtained solid under conditions of a suitable solvent, suitable temperature, and the like.

The compound according to the embodiment of the present disclosure represented by the general formula (1) can be purified by purification by column chromatography; adsorption purification with silica gel, activated carbon, activated clay, or the like; recrystallization with a solvent, or a known method such as a crystallization method. Further, for compound identification and physical property evaluation analysis, UV-visible absorption spectrum analysis (UV-Vis), thermogravimetry-differential thermal analysis (TG-DTA), gas chromatography analysis (GC), nuclear magnetic resonance (NMR) analysis, and the like can be performed.

The compound according to the embodiment of the present disclosure is favorably used in the form of a so-called hair colorant. The compound represented by the general formula (1) is favorably used as a hair dyeing dye, and can be used as a hair dyeing dye containing the compound represented by the general formula (1) by mixing another dye, an additive, components of an auxiliary, or the like therewith. An embodiment of the present disclosure suitable for the hair dyeing dye is a hair dyeing composition, and includes a hair dyeing dye containing a compound represented by the general formula (1), at least one auxiliary selected from the group consisting of a wetting agent, a swelling agent, a penetrating agent, a solvent, a pH adjusting agent, a surfactant, a fragrance, and a thickener, and water.

Examples of the wetting agent include glycerin, propylene glycol, sorbitols, 1,3-butylene glycol, and polyethylene glycols. In the case of using a wetting agent, the content of the wetting agent is favorably 0.1 to 20% by mass, and more favorably 0.5 to 10% by mass, on the basis of the total amount of the hair dyeing composition.

Examples of the swelling agent include an alkaline aqueous solution containing ammonia (ammonium hydroxide) or monoethanolamine (MEA). In the case of using a swelling agent, the content of the swelling agent is favorably 0.1 to 20% by mass, and more favorably 0.5 to 10% by mass, on the basis of the total amount of the hair dyeing composition.

Further, examples of the penetrating agent and the solvent include: a monohydric alcohol having an alkyl group and 1 to 6 carbon atoms, such as ethanol, 1-propanol, 2-propanol, 1-butanol, 2-butanol, and butoxyethanol; a polyhydric alcohol having an alkyl group and 3 to 8 carbon atoms, such as propanediol, butanediol, pentanediol, hexanediol, hexanetriol, heptanediol, heptanetriol, octanediol, octanetriol, isoprene glycol, propylene glycol, glycerin, and diethylene glycol monoethyl ether, or ethers thereof; N-alkylpyrrolidone that is liquid at room temperature (25±2° C.), such as N-methyl-2-pyrrolidone, N-ethyl-2-pyrrolidone, N-propyl-2-pyrrolidone, N-butyl-2-pyrrolidone, and N-cyclohexyl-2-pyrrolidone; an alkylene carbonate (lower alkylene carbonate) such as an ethylene carbonate and a propylene carbonate; and an aromatic alcohol such as benzyloxyethoxyethanol, benzyl alcohol, benzyloxyethanol, cinnamyl alcohol, p-anisyl alcohol, p-methylbenzyl alcohol, phenoxyethanol, phenoxyisopropanol, 2-benzylethanol, and β-phenylethyl alcohol. Among these, aromatic alcohol or N-alkylpyrrolidone is favorable, and benzyl alcohol, benzyloxyethoxyethanol, and benzyloxyethanol are more favorable. In the case of using a penetrating agent or a solvent, the content thereof is favorably 2 to 40% by mass, and more favorably 5 to 20% by mass, on the basis of the total amount of the hair dyeing composition.

Examples of the pH adjusting agent include an acid such as phosphoric acid, lactic acid-sodium lactate, and citric acid-sodium citrate, and a base such as ammonia water, sodium hydroxide, potassium hydroxide, and sodium carbonate. In the case of using a pH adjusting agent, the content of the pH adjusting agent is favorably 0.1 to 10% by mass, and more favorably 0.5 to 5% by mass, on the basis of the total amount of the hair dyeing composition.

As the surfactant, a cationic surfactant or a nonionic surfactant is mainly used specific examples of the surfactant include, but not limited to, a silicone compound such as polysiloxane, polyoxyethylene alkyl ether, polyoxyethylene fatty acid ester, polyglycerol fatty acid ester, aliphatic amine and a quaternary ammonium salt thereof (such as trimethylstearyl ammonium chloride), sugar alcohol ethers such as sorbitol alkyl ether, and polyoxyethylene sorbitan fatty acid ester. Among these, polyoxyethylene sorbitan fatty acid ester is favorable. Using polyoxyethylene sorbitan fatty acid ester further improves the effect of reducing skin contamination (skin contamination prevention performance).

As polyoxyethylene sorbitan fatty acid ester, at least one selected from the group consisting of polyoxyethylene sorbitan monolaurate, polyoxyethylene sorbitan monopalmitate, polyoxyethylene sorbitan monostearate, and polyoxyethylene sorbitan monooleate is favorably used.

In the case of using a surfactant, the content of the surfactant is favorably 0.1 to 20% by mass, and more favorably 0.5 to 10% by mass, on the basis of the total amount of the hair dyeing composition, from the viewpoint of reducing the skin contamination.

Examples of the fragrance include vanillin, cinnamyl alcohol, heliotropin, coumarin, 2-methyl-3-(3,4-methylenedioxy-phenyl)-propanal, 4-(4-hydroxyphenyl)-2-butanone, benzaldehyde, anise alcohol, 3,4-dimethoxybenzaldehyde, heliotropyl acetate, phenylacetaldehyde dimethyl acetal, phenoxyethyl alcohol, phenylacetaldehyde glyceryl acetal, furaneol, sugar lactone, maltol, ethyl maltol, ethyl diglycol, benzyl acetate, linalool, camphor, turpineol, citronellol, geraniol, 2,6-nonadienal, methyl octyl carbonate, 3,7-dimethyl-2,6-octadienal, and nonanal. In the case of using a fragrance, the content of the fragrance is favorably 0.00001 to 2% by mass, on the basis of the total amount of the hair dyeing composition.

Examples of the thickener include guar gum and a derivative thereof, hydroxyethyl cellulose, xanthan gum, collagen, gelatin, a carboxymethylcellulose sodium salt, Carbopol (registered trademark), sodium alginate, gum arabic, a cellulose derivative, and a thickener derived from poly(ethylene oxide). These thickeners have the effect of increasing the viscosity of the hair dyeing composition to form a gel that is easy to handle. In the case of using a thickener, the content thereof is favorably 0.1 to 20% by mass, and more favorably 0.5 to 10% by mass, on the basis of the total amount of the hair dyeing composition.

The water used in the hair dyeing composition according to the embodiment of the present disclosure is not particularly limited, and ion exchange water, purified water, clean water, or the like can be used.

The hair dyeing dye including the compound represented by the general formula (1) according to the embodiment of the present disclosure itself is excellent in hair dyeing power and fastness as a hair dyeing dye, and is capable of dyeing hair uniformly. Further, toning from yellow to brown to black is also possible by combining a hair dyeing dye for other colors and the hair dyeing dye including the compound represented by the general formula (1).

Examples of the basic dye to be combined include a direct dye having an amino group or substituted amino group in the molecule. Specific Examples thereof include Red No. 213 (C.I. Basic Violet 10, Rhodamine B), Red No. 214 (C.I. Basic Violet, Rhodamine B acetate); C.I. Basic Blue 7, 9, 26, 75, 99; C.I. Basic Red 2, 22, 51, 76; C.I. Basic Yellow 57, 87; C.I. Basic Orange 31; C.I. Basic Brown 16, 17; and C.I. Basic Violet 2, 3, 4, 14. Note that "C.I." indicates a color index.

Examples of the HC dye to be combined include a direct dye having a nitro group in the molecule. Specific examples thereof include C. I. HC Blue 2, 15; C. I. HC Red 1, 3, 7, 11, 13; C. I. HC Yellow 2, 4, 5, 9, 11, 13, C. I. HC Orange 1, 2; C. I. HC Violet 1, 2; and 4-hydroxypropyl amino-3-nitrophenol.

In the embodiment of the hair dyeing composition according to the present disclosure, it is favorable that the content of the hair dyeing dye including the compound represented by the general formula (1) is 0.001 to 5% by mass, on the basis of the total amount of the hair dyeing composition, and the other portion includes at least one auxiliary selected from the group consisting of a wetting agent, a swelling agent, a penetrating agent, a solvent, a pH adjusting agent, a surfactant, a fragrance, and a thickener, and water. In the case where the content of the hair dyeing dye is less than 0.001% by mass, it is difficult to achieve the effect of color tone maintenance and uniform dyeability, and improvement of the effect of dyeing and the like is reduced even if the hair dyeing dye is added in an amount exceeding 5% by mass. The content of the hair dyeing dye is favorably 0.01 to 5% by mass, and more favorably 0.05 to 2% by mass, on the basis of the total amount of the hair dyeing composition.

The pH value of the hair dyeing composition according to the embodiment of the present disclosure is favorably 4 to 9, and more favorably 5 to 7. The pH value of the hair dyeing composition can be adjusted by a known method. However, it is favorably to perform the adjustment using the pH adjusting agent such as citric acid monohydrate and trisodium citrate dihydrate. That is, for example, in the case of preparing the hair dyeing composition of pH 6, after dissolving citric acid monohydrate and trisodium citrate dihydrate in water and preparing an aqueous solution of pH 6 in advance, the hair dyeing dye including the compound represented by the general formula (1) is added to the aqueous solution, and another additive (auxiliary or the like) is added thereto as necessary, thereby obtaining a hair dyeing composition of pH 6.

A known cosmetic ingredient may be added to the hair dyeing composition according to the embodiment of the present disclosure as long as the effects of the present disclosure are not hindered. Examples of the cosmetic ingredient that can be added include higher alcohol, petrolatum, a polyhydric alcohol, esters, a preservative, a bactericide, a silicone derivative, and a water-soluble polymer.

As a method of dyeing hair using the hair dyeing composition according to the embodiment of the present disclosure, specifically, by causing hair to be dyed such as human hair and livestock hair to be brought into contact with the hair dyeing composition according to the embodiment of the present disclosure, the hair can be dyed. The hair dyeing temperature is favorably 5 to 60° C., and more favorably 15 to 45° C. considering that the hair dyeing is performed near the scalp. The hair dyeing time is favorably 5 to 60 minutes, and more favorably 10 to 30 minutes.

After hair dyeing, post-treatment such as washing with water and drying is usually performed. The washing with water only needs to be performed until the color of the hair dye is not completely eluted. For example, the washing with water is performed by rinsing with running water at 5 to 40° C. and 5 to 15 L/min for 0.5 to 2 minutes. Drying after the washing with water may be natural drying (usually at 5 to 40° C. for 10 minutes to 10 hour). As necessary, a hot air dryer (usually at 40 to 60° C. for 10 minutes to 10 hours) may be used.

Further, soaping may be performed after the washing with water. The soaping is performed, for example, by performing washing usually at a temperature of 15 to 50° C. for 1 to 10 minutes using an appropriate amount of a soaping liquid (mixture of shampoo and warm water), and then performing washing with water until the soaping liquid is completely removed.

With the above-mentioned embodiment, the hair dyeing dye and the hair dyeing composition including the compound according to the embodiment of the present disclosure are capable of exhibiting an excellent dyeing affect for any of hair colorings, hair manicures, and hair color treatments. In particular, the hair dyeing dye and the hair dyeing composition are capable of exhibiting the effect also for hair color treatments that are considered to have weak dyeing power.

Example

Hereinafter, the present disclosure will be described in detail on the basis of Examples. The present disclosure is not limited to the following Examples.

<Method of Evaluating Test Specimen>

In the following Examples and Comparative Examples, obtained test specimens were evaluated using a spectrocolorimeter (J5555, manufactured by COLOR TECHNO SYSTEM CORPORATION). Further, the hair dyeing concentration ($K/S_d$) was calculated in accordance with the following procedure. The reflectance ($R_\lambda$) at each wavelength ($\lambda$) of the test specimen before hair dyeing (white hair) and after hair dyeing (dyed hair) was measured by a spectrocolorimeter, and the optical density (K/S) was calculated using the following Kubelka-Munk equation. The value obtained by subtracting the optical density (K/S) of white hair from the optical density (K/S) of dyed hair was obtained as the hair dyeing concentration ($K/S_d$).

Kubelka-Munk equation:

$$K/S=\Sigma(1-R_\lambda)^2/2R_\lambda$$

$R_\lambda$: Reflectance at wavelength ($\lambda$)
$\lambda$: 400 to 700 nm (10 nm interval)

For the color tone, L*, a* and b* were measured with a spectrocolorimeter using the CIE L*a*b* color system. The L* represents lightness. The larger the lightness, the smaller the coloring intensity. The a* and b* are chromaticities indicating hue and saturation. The a* corresponds to the red/green axis, plus is red, and minus is green. The b* corresponds to the yellow/blue axis, plus is yellow, and minus is blue.

Further, the color tone (L*, a*, and b*) for each test specimen before and after hair dyeing was measured, and a color difference ΔE* and a hue difference ΔH* were calculated from values of differences ΔL*, Δa* and Δb* between the color tone values in accordance with the following equations.

$$\Delta E^*=\{(\Delta L^*)^2+(\Delta a^*)^2+(\Delta b^*)^2\}^{1/2}$$

$$\Delta H^*=\{(\Delta a^*)^2+(\Delta b^*)^2\}^{1/2}$$

The sweat resistance was evaluated by obtaining the $K/S_d$ ratio (residual rate %), the color difference (ΔE*), and the hue difference (ΔH*) of the following sweat resistance test specimens relative to untested specimens. Note that the ΔE* and ΔH* were obtained by measuring the L*, a* and b* with the spectrocolorimeter JS555 manufactured by manufactured by COLOR TECHNO SYSTEM CORPORATION and in accordance with the following formulae. A smaller ΔE* indicates less discoloration, and a smaller ΔH* indicates less hue change and excellent sweat resistance.

$$\Delta E^*=\{(\Delta L^*)^2+(\Delta a^*)^2+(\Delta b^*)^2\}^{1/2}$$

$$\Delta H^*=\{(\Delta a^*)^2+(\Delta b^*)^2\}^{1/2}$$

Hereinafter, an embodiment of the present disclosure will be specifically described with reference to Examples. However, the present disclosure is not limited to the following Examples.

Synthesis Example 1

Synthesis of Compound (A-1)

Fifty g of C.I. Basic Blue 75, 500 mL of MeOH, and 250 mL of water were added in the reaction vessel and heated to 60° C., and C.I. Basic Blue 75 was dissolved. Forty five point seven g of sodium lauroyl glutamate was added to this solution and stirred at 60° C. for 2 hours. Methanol was distilled off under reduced pressure, and the precipitated solid was filtered off from water. The operation of stirring the obtained solid in 500 mL of denatured ethanol at 60° C. for 1 hour, removing the insoluble matter by filtration, and distilling off the solvent under reduced pressure was performed twice, and thus, a compound (54.7 g, 62% yield) represented by the following formula (A-1) was obtained.

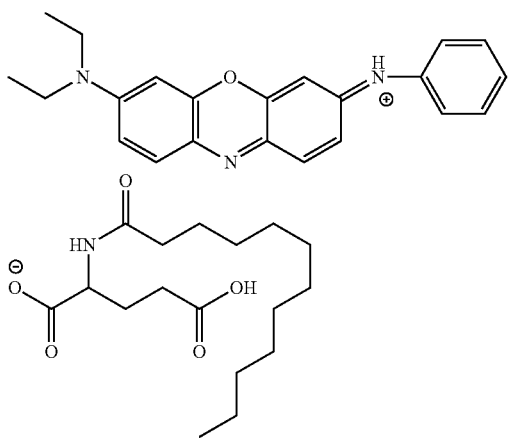

(A-1)

NMR measurement of the compound (A-1) was performed, and the following results were obtained.

$^1$H NMR (600 MHz, CD$_3$OD): δ (ppm)=0.89 (3H, t, J=6.9 Hz), 1.36 (6H, t, J=7.6 Hz), 1.60-1.62 (18H, m), 2.23 (2H, t, J=6.2 Hz), 2.28-2.32 (2H, m), 3.82 (4H, m), 4.26-4.28 (1H, m), 7.01 (1H, d, J=2.8 Hz), 7.05 (1H, d, J=2.8 Hz), 7.31-7.34 (2H, m), 7.39-7.40 (2H, m), 7.48-7.52 (3H, m), 7.78-7.80 (2H, m).

Synthesis Example 2

Synthesis of Compound (A-2)

Ten g of C.I. Basic Red 51 and 200 mL of water were added in a reaction vessel and heated to 60° C., and C.I. Basic Red 51 was dissolved. Eighteen point nine g of sodium lauroyl glutamate was added to this solution and stirred at 60° C. for 1 hour. The precipitated solid and the solution were separated by filtration, and the obtained solid was stirred in 100 mL of denatured ethanol at 60° C. for 1 hour. After that, the insoluble matter was removed by filtration, and then, the solvent was distilled off under reduced pressure to obtain a compound (11.8 g, 57% yield) represented by the following formula (A-2).

[Chem. 19]

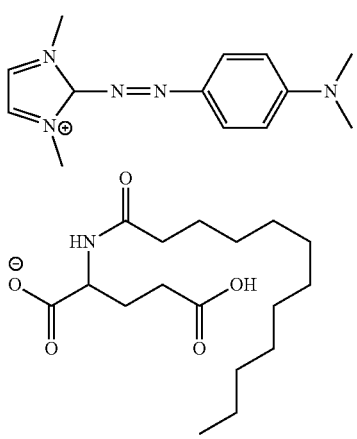

(A-2)

NMR measurement of the compound (A-2) was performed, and the following results were obtained.

$^1$H NMR (600 MHz, CD$_3$OD): δ (ppm)=0.89 (3H, t, J=6.9 Hz), 1.60-1.62 (18H, m), 2.23 (2H, t, J=6.2 Hz), 2.28-2.32 (2H, m), 3.26 (6H, s), 4.04 (6H, s), 4.26-4.28 (1H, m), 6.94 (2H, d, J=8.9 Hz), 7.50 (2H, s), 7.97 (2H, d, J=8.9).

Synthesis Example 3

Synthesis of Compound (A-3)

Ten g of C.I. Basic Violet 2 and 300 mL of water were added in the reaction vessel and heated to 60° C., and C.I. Basic Violet 2 was dissolved. Eighteen point nine g of sodium lauroyl glutamate was added to this solution and stirred at 60° C. for 1 hour. The solution portion was removed, and the obtained solid was stirred in 500 mL of denatured ethanol at 60° C. for 1 hour. After the insoluble matter was removed by filtration, the solvent was distilled off under reduced pressure. The obtained solid was stirred in 100 mL of denatured ethanol at 60° C. for 1 hour, the insoluble matter was removed by filtration, and the solvent was distilled off under reduced pressure to obtain a compound (15.9 g, 89.7% yield) represented by the following formula (A-3).

[Chem. 20]

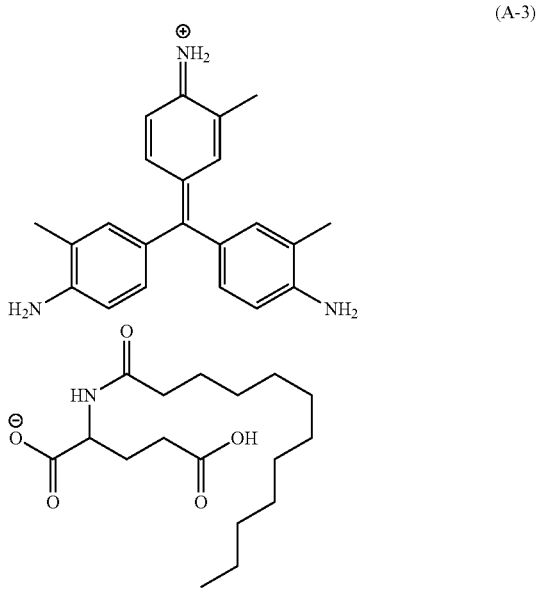

(A-3)

NMR measurement of the compound (A-3) was performed, and the following results were obtained.

$^1$H NMR (600 MHz, CD$_3$OD): δ (ppm)=0.89 (3H, t, J=6.9 Hz), 1.60-1.62 (18H, m), 2.11 (9H, S), 2.23 (2H, t, J=6.2), 2.28-2.32 (2H, m), 4.26-4.28 (1H, m), 6.78 (3H, d, J=8.3 Hz), 6.93 (3H, s), 6.99 (3H, d, J=8.3 Hz).

Synthesis Example 4

Synthesis of Compound (A-4)

Ten g of C.I. HC Blue 15 and 350 mL of water were added in the reaction vessel and heated to 60° C., and C.I. HC Blue 15 was dissolved. Seven point zero g of sodium lauroyl glutamate was added to this solution and stirred at 60° C. for 2 hours. The solid obtained by removing the solution portion was stirred 200 mL of denatured ethanol at 60° C. for 1 hour, the insoluble matter was removed by filtration, and the solvent was distilled off under reduced pressure. The obtained solid was stirred in 100 mL of denatured ethanol at 60° C. for 1 hour, the insoluble matter was removed by filtration, and the solvent was distilled off under reduced pressure to obtain a compound (10.6 g, 73% yield) represented by the following formula (A-4).

[Chem. 21]

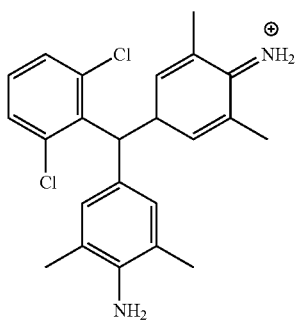

(A-4)

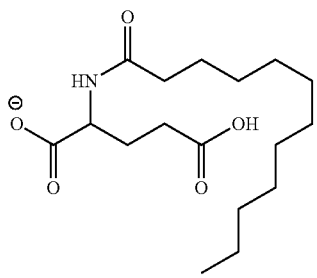

NMR measurement of the compound (A-4) was performed, and the following results were obtained.

$^1$H NMR (600 MHz, CD$_3$OD): δ (ppm)=0.89 (3H, t, J=6.9 Hz), 1.60-1.62 (18H, m), 2.21 (12H, s), 2.23 (2H, t, J=6.2), 2.28-2.32 (2H, m), 4.26-4.28 (1H, m), 7.14 (4H, s), 7.55-7.61 (3H, m).

Synthesis Example 5

Synthesis of Compound (A-5)

Thirty g of C.I. Basic Brown 16 and 300 mL of methanol were added in the reaction vessel and heated to 60° C., and C.I. Basic Brown 16 was dissolved. Twenty nine point five g of sodium lauroyl glutamate was added to this solution and stirred at 60° C. for 2 hours. The solid obtained by distilling off the solvent under reduced pressure is stirred in 300 mL of denatured ethanol at 60° C. for 1 hour, and the insoluble matter was removed by filtration. The operation of stirring the solid obtained by distilling off the solvent under reduced pressure in 150 mL of water at 60° C. for 1 hour and removing the solution by filtration was repeated three times, and the obtained solid was dried to obtain a compound (16.0 g, 29.3% yield) represented by the following formula (A-4).

[Chem. 22]

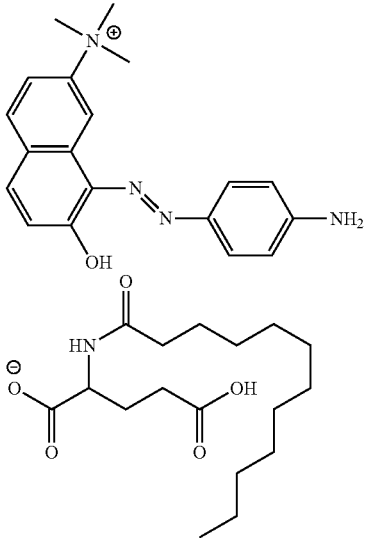

(A-5)

NMR measurement of the compound (A-5) as performed, and the following results were obtained.

$^1$H NMR (600 MHz, CD$_3$OD): δ (ppm)=0.89 (3H, t, J=6.9 Hz), 1.60-1.62 (18H, m), 2.23 (2H, t, J=6.2 Hz), 2.28-2.32 (2H, m), 3.83 (9H, s), 4.26-4.28 (1H, m), 7.73 (2H, d, J=8.9 Hz), 7.82 (1H, d, J=8.9 Hz), 7.92 (1H, d, J=9.6 Hz), 8.01 (1H, d, J=9.6 Hz), 9.07 (1H, s).

Example 1

<Hair Dyeing>

Sixteen point five mg of the compound (A-3) as a hair dyeing dye, 100 mg of ethanol, 100 mg of trimethylstearyl ammonium chloride as a surfactant, 200 mg of hydroxyethyl cellulose as a thickener, 9.53 g of pH 6 aqueous solution as a pH adjusting agent (citric acid. H$_2$O/citric acid.tri-Na.2H$_2$O/water (1:11:988) aqueous solution) were mixed to prepare a dyeing gel.

Subsequently, Human White hair 100% BM-W manufactured by Beaulax Co., Ltd. was used as hair to be dyed. Two parts by mass of the dyeing gel was taken with respect to 1 part by mass of the hair and applied to the hair uniformly using a comb, and the hair was dyed at 40° C. for 10 minutes and washed with water.

From the compound (A-3), a test specimen that had sufficient water solubility for hair dyeing and favorable foaming property during hair dyeing while maintaining the smooth hair with no hair roughness and no hair irregularity during washing and after drying could be obtained.

By the above-mentioned <Method of Evaluating Test Specimen>, the hair dyeing concentration (K/S$_d$) and the color tone of the test specimen before the test were measured. The results are shown in Table 1.

<Sweat Resistance Test>

Treatment using the following artificial sweat (manufactured by Hayashi Pure Chemical Ind., Ltd.) was performed on the sufficiently dried test specimen, and then the test specimen was washed with water.

Treatment using artificial sweat:

Artificial sweat component (Acidic) 0.05% L-histidine hydrochloride monohydrate
0.50% sodium chloride
0.22% sodium dihydrogen phosphate dihydrate 0.005% sodium hydroxide aqueous solution (pH 5.5)
(Basic) 0.05% L-histidine hydrochloride monohydrate
0.50% sodium chloride
0.50% disodium hydrogen phosphate 12 hydrate
0.007% sodium hydroxide aqueous solution (pH 8.0)
Bath ratio: 1:10 (10 parts by mass of treatment liquid per 1 part by mass of dyed hair)
Treatment temperature: 40° C.
Treatment time: 10 minutes The dyeing concentration ($K/S_d$) of the hair test specimen on which the treatment using artificial sweat had been performed under the above conditions was measured to evaluate the residual rate (%). Similarly, the color tone was measured and the hue difference ($\Delta H$) before and after the test was evaluated. The results are collectively shown in Table 1.

TABLE 1

| | | Before test | Sweat resistance test (acidic) | | Sweat resistance test (basic) | |
|---|---|---|---|---|---|---|
| | Compound | Dyeing concentration (K/Sd) | Residual rate | Hue difference $\Delta H$ | Residual rate | Hue difference $\Delta H$ |
| Example 1 | (A-3) | 129.7 | 99.9% | 1.06 | 83.3% | 1.07 |
| Comparative Example 1 | Basic Violet 2 | 81.2 | 97.5% | 1.03 | 74.7% | 1.02 |
| Example 2 | (A-4) | 65.4 | 96.5% | 0.97 | 79.6% | 0.99 |
| Comparative Example 2 | HC Blue 15 | 50.6 | 89.5% | 0.93 | 97.7% | 1.02 |
| Example 3 | (A-5) | 72.2 | 64.1% | 0.87 | 91.0% | 0.97 |
| Comparative Example 3 | Basic Brown 16 | 60.7 | 85.8% | 0.87 | 73.4% | 0.89 |

Example 2 and Example 3

The hair dyeing, the hair dyeing concentration measurement, and the sweat resistance test were performed in the same way as in Example 1 except that the compounds (A-4) and (A-5) were used instead of the compound (A-3) in Example 1. From the obtained test specimen, similarly to Example 1, a test specimen that had sufficient water solubility for hair dyeing and favorable foaming property during hair dyeing while maintaining the smooth hair with no hair roughness and no hair irregularity during washing and after drying could be obtained. The results of the hair dyeing concentration measurement and sweat resistance test are collectively shown in Table 1.

Comparative Examples 1 to 3

The hair dyeing, the hair dyeing concentration measurement, and the sweat resistance test were performed in the same way as in Example 1 except that C.I. Basic Violet 2, C.I. HC Blue 15, and C.I. Basic Brown 16, which are dyes that do not belong to the compound according to the embodiment of the present invention, were used instead of the compound (A-1) in Example 1. Note that the concentration of each of the dyes in the hair dyeing compositions used in Example 1 and Comparative Example 1, Example 2 and Comparative Example 2, and Example 3 and Comparative Example 3 described above is adjusted so that the mass of the dye (Only components corresponding to coloring components, excluding non-coloring components) per unit mass of the hair to be colored is equal (actually, the dye concentration was adjusted by measuring the absorbance of the dye gel solutions of Examples and Comparative Examples). The results are collectively shown in Table 1 ("C.I." of the compounds in the Table is omitted).

From the results shown in Table 1, it has been found that those using the hair dyeing dye and the hair dyeing composition containing the compound according to the embodiment of the present disclosure have higher hair dyeing concentration and higher hair dyeing power than those using existing dyes. In addition, from the results of the acidic and basic sweat resistance tests, it has been found that the residual rate of the hair dyeing concentration after the test is higher than that of the dye according to Comparative Example and the change in hue after the test is equivalent to that of the existing one. Further, regarding the water solubility, foaming property, presence or absence of hair roughness, and maintaining the smooth hair during washing and after drying, those using the hair dyeing composition according to Examples have achieved the results equivalent to those in Comparative Examples.

INDUSTRIAL APPLICABILITY

In accordance with the compound and the hair dyeing dye according to the present disclosure, it is possible to provide a hair dyeing composition that has an excellent hair dyeing power, favorable water solubility and foaming property, and excellent sweat resistance, and suppress the fading of dyed hair while maintaining the smooth hair with no hair roughness and no hair irregularity during washing and after drying.

It should be understood by those skilled in the art that various modifications, combinations, sub-combinations and alterations may occur depending on design requirements and other factors insofar as they are within the scope of the appended claims or the equivalents thereof.

What is claimed is:

1. A compound represented by the following general formula (1),

[Chem. 1]

$$(X)(Z) \qquad (1)$$

(wherein, X represents a basic dye having at least one amino group having 0 to 20 carbon atoms which may have a substituent, and
Z represents a non-coloring anion including an amino acid).

2. The compound according to claim 1, wherein
X in the general formula (1) represents a basic dye represented by the following general formula (2),

[Chem. 2]

$$R^1-N=N-R^2 \quad (2)$$

(wherein, $R^1$ and $R^2$ each independently represent an amino group having 0 to 20 carbon atoms which may have a substituent, a linear or branched alkenyl group having 2 to 20 carbon atoms which may have a substituent, an aromatic hydrocarbon group having 6 to 30 carbon atoms which may have a substituent, or a heterocyclic group having 2 to 30 carbon atoms which may have a substituent).

3. The compound according to claim 1, wherein

X in the general formula (1) represents a basic dye represented by the following general formula (3),

[Chem. 3]

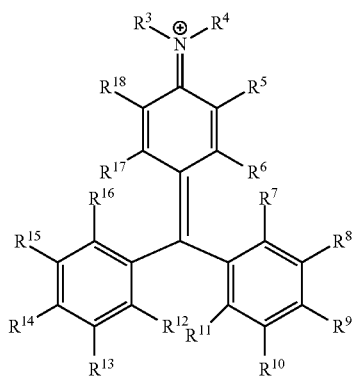

(3)

(wherein, $R^3$ to $R^{18}$ each independently represent —H, a halogen atom, —NO$_2$, —NO, —CN, —OH, an amino group having 0 to 20 carbon atoms which may have a substituent, a linear or branched alkenyl group having 2 to 20 carbon atoms which may have a substituent, a linear or branched alkyl group having 1 to 20 carbon atoms which may have a substituent, a cycloalkyl group having 3 to 20 carbon atoms which may have a substituent, a linear or branched alkoxy group having 1 to 20 carbon atoms which may have a substituent, a cycloalkoxy group having 3 to 20 carbon atoms which may have a substituent, an acyl group having 1 to 20 carbon atoms which may have a substituent, an aromatic hydrocarbon group having 6 to 30 carbon atoms which may have a substituent, or a heterocyclic group having 2 to 30 carbon atoms which may have a substituent, and adjacent groups of $R^3$ to $R^{18}$ may be bonded to each other to form a ring).

4. The compound according to claim 1, wherein

X in the general formula (1) represents a basic dye represented by the following general formula (4),

[Chem. 4]

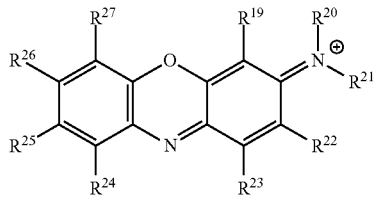

(4)

(wherein, $R^{19}$ to $R^{27}$ each independently represent —H, a halogen atom, —NO$_2$, —NO, —CN, —OH, an amino group having 0 to 20 carbon atoms which may have a substituent, a linear or branched alkenyl group having 2 to 20 carbon atoms which may have a substituent, a linear or branched alkyl group having 1 to 20 carbon atoms which may have a substituent, a cycloalkyl group having 3 to 20 carbon atoms which may have a substituent, linear or branched alkoxy group having 1 to 20 carbon atoms which may have a substituent, a cycloalkoxy group having 3 to 20 carbon atoms which may have a substituent, acyl group having 1 to 20 carbon atoms which may have a substituent, aromatic hydrocarbon group having 6 to 30 carbon atoms which may have a substituent, or a heterocyclic group having 2 to 30 carbon atoms which may have a substituent, and adjacent groups of $R^{19}$ to $R^{23}$ and $R^{24}$ to $R^{27}$ may be bonded to each other to form a ring).

5. The compound according to claim 1, wherein

X in the general formula (1) represents a basic dye represented by the following general formula (5),

[Chem. 5]

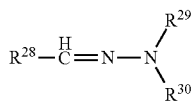

(5)

(wherein, $R^{28}$ to $R^{30}$ each independently represent an amino group having 0 to 20 carbon atoms which may have a substituent, a linear or branched alkenyl group having 2 to 20 carbon atoms which may have a substituent, a linear or branched alkyl group having 1 to 20 carbon atoms which may have a substituent, a cycloalkyl group having 1 to 20 carbon atoms which may have a substituent, a linear or branched alkoxy group having 1 to 20 carbon atoms which may have a substituent, a cycloalkoxy group having 3 to 20 carbon atoms which may have a substituent, an acyl group having 1 to 20 carbon atoms which may have a substituent, an aromatic hydrocarbon group having 6 to 30 carbon atoms which may have a substituent, or a heterocyclic group having 2 to 30 carbon atoms which may have a substituent, and $R^{29}$ and $R^{30}$ may be bonded to each other to form a ring).

6. The compound according to claim 1, wherein
the non-coloring anion including an amino acid represented by Z in the general formula (1) is an amino acid anionic surfactant.

7. A hair dyeing dye including the compound according to claim 1.

8. A hair dyeing composition, comprising:
the hair dyeing dye according to claim 7;
an auxiliary selected from the group consisting of a wetting agent, a swelling agent, a penetrating agent, a solvent, a pH adjusting agent, a surfactant, a fragrance, and a thickener; and
water.

9. The compound according to claim 2, wherein
the non-coloring anion including an amino acid represented by Z in the general formula (1) is an amino acid anionic surfactant.

10. The compound according to claim 3, wherein
the non-coloring anion including an amino acid represented by Z in the general formula (1) is an amino acid anionic surfactant.

11. The compound according to claim 4, wherein
the non-coloring anion including an amino acid represented by Z in the general formula (1) is an amino acid anionic surfactant.

12. The compound according to claim 5, wherein
the non-coloring anion including an amino acid represented by Z in the general formula (1) is an amino acid anionic surfactant.

* * * * *